US005585347A

United States Patent [19]
Meier et al.

[11] Patent Number: 5,585,347
[45] Date of Patent: Dec. 17, 1996

[54] METHODS FOR THE DETERMINATION AND ADJUSTMENT OF PROLACTIN DAILY RHYTHMS

[75] Inventors: Albert H. Meier, Baton Rouge, La.; Anthony H. Cincotta, Andover, Mass.

[73] Assignees: Ergo Science Incorporated, Newport, R.I.; Board of Supervisors of Louisiana State Univerisity and Agricultural and Mechanical College, Baton Rouge, La.

[21] Appl. No.: 995,292

[22] Filed: Dec. 22, 1992

Related U.S. Application Data

[63] Continuation-in-part of Ser. No. 719,745, Jun. 24, 1991, Pat. No. 5,344,832, which is a continuation-in-part of Ser. No. 463,327, Jan. 10, 1990, abandoned, which is a continuation-in-part of Ser. No. 192,332, May 10, 1988, abandoned.

[51] Int. Cl.$^6$ ................................ A61K 38/00
[52] U.S. Cl. .................. 514/12; 436/87; 436/811; 514/250; 514/288; 514/338; 514/866
[58] Field of Search .................. 436/71, 87, 811; 514/250, 288, 866, 338, 12

[56] References Cited

U.S. PATENT DOCUMENTS

| | | | |
|---|---|---|---|
| 4,219,555 | 8/1980 | Rucman | 424/250 |
| 4,239,763 | 12/1980 | Milavec | 424/261 |
| 4,659,715 | 4/1987 | Meier | 514/288 |
| 4,749,709 | 6/1988 | Meier | 514/288 |
| 4,783,469 | 11/1988 | Meier | 514/288 |
| 5,006,526 | 4/1991 | Meier | 514/288 |

FOREIGN PATENT DOCUMENTS

| | | |
|---|---|---|
| 890369 | 9/1980 | Japan . |
| PCT/US92/05074 | 6/1992 | WIPO . |
| PCT/US92/11166 | 12/1992 | WIPO . |

OTHER PUBLICATIONS

Iranhanesh et al. "Attenuated Pulsatile Release of Prolactin in Men with Insulin–Dependent Diabetes Mellitus" 1990 pp. 73–77.
Haisenleder et al. "The Effect of Dopamin Antagonists and/or VIP on TRH or VIP Induce Prolactin Release" 1988 pp. 341–349.
Marken et al. "Management of Psychotropic–induced Hyperprolactinemia" Oct. 1992 pp. 851–855.
Cassar, J. et al. "Bromocriptine Treatment of Acromegaly," *Metabolism* 26: 539–546 (1977).
Dolocek, R. et al. "Bromocriptine and glucose tolerance in acromegalics," *Pharmatherapeutica* 3: 100–106 (1982).
Eskildsen, P. C. et al. "Long–Term Treatment of Acromegaly with Bromocriptine," *Acta Endocr.* 87: 687–700 (1978).
Steinbeck, K. and J. R. Turtle, "Treatment of Acromegaly-with Bromocryptine," *Aust. N. Z. J. Med.* 9: 217–224 (1979).

(List continued on next page.)

*Primary Examiner*—Donald E. Czaja
*Assistant Examiner*—Lien Tran
*Attorney, Agent, or Firm*—Darby & Darby, P.C.

[57] ABSTRACT

Disclosed are methods for detecting abnormalities in prolactin daily rhythms. The methods involve comparing a prolactin profile of a vertebrate (including a human) subject being tested that has been compiled over a predetermined period to a predetermined standard prolactin profile for healthy subjects. The method also involves determining whether the vertebrate subject has an abnormal daily prolactin rhythm by ascertaining whether (i) at any point during waking hours the prolactin level of the subject being tested is greater than 1 SEM above the normal prolactin profile of said healthy subjects, and/or (ii) at any point during sleeptime the prolactin level of the subject being tested is at least 1 SEM lower than the normal prolactin profile of said healthy subjects. Also provided are methods for determining adjustments needed to an abnormal prolactin profile (or daily rhythm) to cause it to conform to the prolactin profile (or rhythm) of a healthy subject, and methods for effecting such adjustments.

48 Claims, 5 Drawing Sheets

OTHER PUBLICATIONS

Wass, J. A. H. et al. "An Assessment of Glucose Intolerance In Acromegaly and Its Response to Medical Treatment," *Clin. Endocr.* 12: 53–59 (1980).
Martin et al., *Neuroendocrinology* 52: 9–14, 1990.
Martin et al., *The Condor* 75: 369–374, 1973.
Meier et al., *Science* 173: 1240–42, 1971.
Meier et al., *Gen. & Comp. Endocrin.* 17: 311–8, 1971.
Barnett et al., *Postgraduate Med. J.* 56:11–14, 1980.
Bartness et al., *J. Exp. Zoology* 244:437–454, 1987.
Berle, *Acta endocr. Suppl.* 173, Abstract No. 104, 1973.
Burns, et al., *Rev. Chronopharmacology* 5:57–60, 1988.
Chemical Abstracts, vol. 109, No. 9, 66888w, Aug. 29, 1988.
Cincotta et al., *Amer. J. of Physiol.* 285–93, Feb. 1993.
Cincotta et al., *Life Sciences* 45:2247–2254, 1989.
Cincotta et al., *Ann Nutr Metab* 33:305–14, 1989.
Cincotta et al., *Horm. Metabol. Res.* 21:64–68, 1989.
Cincotta et al., *J. Endocrinology* 120:385–391, 1989.
Cincotta et al., *Experientia* 43:416–417, 1987.
Cincotta et al., *J. Endocr.* 106:177–181, 1985.
Cincotta et al., *J. Endocr.* 106:173–176, 1985.
Cincotta et al., *J. Endocr.* 103:141–146, 1984.
Eisemann et al., *J. of Animal Sci.* 59(1)95–104, 1984.
Eisemann et al., *J. of Animal Sci.* 59(1)86–94, 1984.
Gnudi et al., *Acta Diabetologica Latina* 14:119–128, 1977.
Horseman et al., *J. Endocr.* 82:367–372, 1979.
Horseman et al., *General and Comparative Endocrinology* 38:269–274, 1979.
Joseph et al., *J. Exp. Zool.* 178(1):59–62, 1971.
Landgraf et al., *Proc. German Med. Soc.* 82nd Convention, Part 11, Apr. 25–29, 1976.
Lee et al., *J. of Exp. Zool.* 166(3):307–316, 1969.
Meier et al., *Nature* 271:469–471, 1978.
Meier, et al., *Experientia* 48:248–253, 1992.
Meier, *Amer. Zoology*, 15:905–916, 1975.
Meier, *Amer. Scientist* 61(2)184–187, 1973.
Meier, *Gen. & Comp. Endocrin. Supp.* 2:55–62, 1969.
Meier et al., *Gen. & Comp. Endocrin.* 8(1):110–114, 1967.
Meier et al., *Compar. Endocrin.* 141–44, 1978.
Meier et al., *Amer. J. of Physiology* 232(2):E193–E196, 1977.
Meier et al., *Amer. Zool.* 16:649–659, 1976.
Southern et al., *J. Anim. Sci.* 68:931–936, 1990.
Spieler et al., *Gen. & Comparative Endocrinology* 29:156–160, 1976.
Spieler et al., *Life Sciences* 22:255–258, 1977.
Thomas et al., *Semaine des Hopitaux de Paris* 53(34–35): 1857–1862, 1977.
Wheeland, et al., *Comp. Biochem. Physiol.* vol. 53B; 379–385, 1976.
Wilson et al., *Chronobiology Int'l* 6(2):113–121, 1989.3:189–195, 1989.

METHODS FOR THE DETERMINATION AND ADJUSTMENT OF PROLACTIN DAILY RHYTHMS

RELATED APPLICATIONS

This application is a continuation-in-part of U.S. application Ser. No. 719,745 filed Jun. 24, 1991, now U.S. Pat. No. 5,344,832, in turn a continuation-in-part of Ser. No. 463,327, filed Jan. 10, 1990, now abandoned, which is a continuation-in-part of Ser. No. 192,332 filed May 10, 1988, now abandoned, all by Anthony H. Cincotta and Albert H. Meier.

FIELD OF THE INVENTION

This invention relates to a method for the reduction in a subject, vertebrate animal or human, of body fat stores, and reduction of at least one of insulin resistance, hyperinsulinemia, hyperlipidemia and hyperglycemia, and other metabolic diseases, especially those associated with Type II diabetes. In particular the present invention is directed to methods for: (i) normalizing the daily prolactin secretion cycles of a human or vertebrate animal; (ii) diagnosing aberrant daily prolactin secretion cycles of a human or vertebrate animal; and (iii) determining the appropriate adjustments that need to be made to normalize such aberrant prolactin secretion cycles. Such adjustments include the relatively short-term daily administration to the subject of at least one of a prolactin stimulator and/or a prolactin inhibitor at a predetermined time of day (if only one is administered) or at different predetermined times of day (if both are administered). This relatively short-term therapy results in the long-term adjustment of aberrant or abnormal prolactin secretion cycles so that they conform to or simulate normal prolactin secretion cycles. In turn, this adjustment results in reduction and control over an extended time period of one or more metabolic disorders or other disorders dependent (in whole or in part) on the phase of at least one circadian central neural oscillation (which is expressed by the daily prolactin secretion rhythm).

BACKGROUND OF THE INVENTION

Diabetes, one of the most insidious of the major diseases, can strike suddenly or lie undiagnosed for years while attacking the blood vessels and nerves. Diabetics, as a group, are more often afflicted with blindness, heart disease, stroke, kidney disease, hearing loss, gangrene and impotence, than the non-diabetic population. One third of all visits to physicians are occasioned by this disease and its complications, and diabetes and its complications are a leading cause of death in this country.

Diabetes adversely affects the way the body uses sugars and starches which, during digestion, are converted into glucose. Insulin, a hormone produced by the pancreas, makes the glucose available to the body's cells for energy. In muscle, adipose (fat) and connective tissues, insulin facilitates the entry of glucose into the cells by an action on the cell membranes. The ingested glucose is normally converted in the liver to $CO_2$ and $H_2O$ (50%); to glycogen (5%) and to fat (30–40%), which is stored in fat depots. Fatty acids are circulated, returned to the liver and metabolized to ketone bodies for utilization by the tissues. The fatty acids are also metabolized by other organs, e.g., muscle. The net effect of insulin is to promote the storage and use of carbohydrates, protein and fat. Insulin deficiency is a common and serious pathologic condition in man. In Type I diabetes the pancreas produces little or no insulin, and insulin must be injected daily for the survival of the diabetic. In Type II diabetes the pancreas produces some insulin, but the amount of insulin is insufficient, or less than fully effective due to cellular resistance, or both. In either form there are wide-spread abnormalities, but the fundamental defects to which the abnormalities can be traced are (1) a reduced entry of glucose into various "peripheral" tissues and (2) an increased liberation of glucose into the circulation from the liver (increased hepatic glucogenesis). There is therefore an extracellular glucose excess and an intracellular glucose deficiency which has been called "starvation in the midst of plenty". There is also a decrease in the entry of amino acids into muscle and an increase in lipolysis. Thus, as a result of the diabetic condition, elevated levels of glucose in the blood, and prolonged high blood sugar are indicative of a condition which will cause blood vessel and nerve damage. It is believed that obesity, or excess fat deposits, may trigger the onset of diabetes by increasing cellular resistance to insulin. Prior to the onset of diabetes, the pancreas of an obese subject is taxed to produce additional insulin; but eventually, perhaps over several years, insulin productivity falls and diabetes results. Reduction of body fat can improve insulin production, and it is thought avoid cellular insensitivity to insulin.

The reduction of body fat stores on a long term, or permanent basis in domestic animals would obviously be of considerable economic benefit to man, particularly since animals supply a major portion of man's diet; and the animal fat may end up as de novo fat deposits in man, with resulting adverse effects on health. The reduction of body fat stores in man likewise would be of significant benefit, cosmetically and physiologically. Indeed, obesity and insulin resistance, the latter of which is generally accompanied by hyperinsulinemia or hyperglycemia or both, are hallmarks of Type II diabetes. Whereas controlled diet and exercise can produce modest results in the reduction of body fat deposits, no effective treatment has been found for controlling either hyperinsulinemia or insulin resistance. Hyperinsulinemia is a higher-than-normal level of insulin in the blood. Insulin resistance can be defined as a state in which a normal amount of insulin produces a subnormal biologic response. In insulin treated patients with diabetes, insulin resistance is considered to be present whenever the therapeutic dose of insulin exceeds the secretory rate of insulin in normal persons. Insulin resistance is also defined by higher-than-normal levels of insulin i.e., hyperinsulinemia—when present with normal or elevated levels of blood glucose. Despite decades of research on these serious health problems, the etiology of obesity and insulin resistance is unknown.

The principal unit of biological time measurement, the circadian or daily rhythm, is present at all levels of organization. Daily rhythms have been reported for many hormones inclusive of the adrenal steroids. e.g., the glucocorticosteroids, notably cortisol, and prolactin, a hormone secreted by the pituitary. In an early article, discussing the state-of-the-art at that time, it was reported that "Although correlations have been made between hormone rhythms and other rhythms, there is little direct evidence that the time of the daily presence or peak level of hormones has important physiological relevance." See *Temporal Synergism of Prolactin and Adrenal Steroids* by Albert H. Meier, General and Comparative Endocrinology. Supplement 3, 1972 Copyright 1972 by Academic Press, Inc. The article reports that the peak concentration of prolactin occurs at different times of day in lean and fat animals. The article then describes arian physiological responses to prolactin injections given daily for several days. These responses include increases and decreases in body fat stores, dependent on the time of day of the injection. Furthermore the time of day when prolactin injections promote loss of body fat coincides with the time of day when prolactin secretion is greatest in lean birds. Additionally, the time when prolactin injections promote gain of body fat coincides with the time when prolactin secretion is greatest in obese birds. Prolactin was thus found to stimulate fattening only when injected at certain times of the day, and time of the response to prolactin was found to differ between lean animals and fat animals.

In an article titled *Circadian and Seasonal Variation of Plasma Insulin and Cortisol Concentrations in the Syrian Hamster, Mesocricetus Auratus* by Christopher J. de Souza and Albert H. Meier, Chronobiology International, Vol. 4. No. 2. pp 141–151, 1987, there is reported a study of circadian variations of plasma insulin and cortisol concentrations in scotosensitive and scotorefractory Syrian hamsters maintained on short and long periods of daylight to determine possible seasonal changes in their daily rhythms. The baseline concentration of insulin was found to be greater in female than in male scotosensitive hamsters on short daylight periods. These differences it is reported, may account for the observed heavy fat stores in female hamsters kept on short daylight periods. The plasma concentrations of both cortisol and insulin varied throughout the day for the groups of animals tested, but were not equivalent. The circadian variation of insulin and cortisol differed markedly with sex, seasonal condition and day length. Neither the daily feeding pattern or glucose concentration varied appreciably with seasonal condition, or daylight. The time of day, or the season, it is reported do not appear to affect the concentrations in glucose levels. It is postulated that the daily rhythms of cortisol and insulin are regulated by different neural pacemaker systems, and that changes in the phase relations of circadian systems account in part for seasonal changes in body fat stores. The circadian rhythms of prolactin and the glucocorticosteroid hormones, e.g., cortisol, have thus been perceived as having important though far from fully understood roles in regulating daily and seasonal changes in body fat stores and in the organization and integration of total animal metabolism. See *Circadian Hormone Rhythms in Lipid Regulation* by Albert H. Meier and John T. Burns, Amer. Zool. 16:649–659 (1976).

In our prior co-pending patent application Ser. No. 192,332 we have disclosed and claimed methods for regulating lipid metabolism disorders by administering prolactin (or both prolactin and a glucocorticosteroid ("GC")) into the bloodstream of an animal or human on a timed daily basis in an amount and for a period of time sufficient to modify and reset the neural phase oscillation of the prolactin daily rhythm which then increases insulin sensitivity. The prolactin (or prolactin and glucocorticosteroid) injections are timed to create a peak in the subject's daily prolactin (or both prolactin and glucocorticosteroid) secretion profile that coincides in time with the peak prolactin secretion (or prolactin and GC peaks, respectively) of a lean, insulin-sensitive human to increase insulin sensitivity and reduce body fat stores. Injections of the same agent(s) are timed towards the peak prolactin secretion time of an obese subject to achieve fat gain, if desired.

In our co-pending prior application Ser. No. 463,327 we have disclosed and claimed a method of modifying and resetting the neural phase oscillations of the brain which controls both prolactin and GC in an obese animal (or human) by administering a dopamine agohist at a predetermined time of day such that the prolactin (and/or GC) peak(s) of the obese animal (or human) will be phase-shifted to occur at the time that it occurs (they occur) in a lean animal (or human), with the result that at least one of body fat stores, body weight, hyperinsulinemia, or hyperglycemia will be reduced and/or insulin sensitivity will be increased.

In our co-pending prior application Ser. No. 719,745 we have disclosed and claimed enhanced methods for modifying and resetting the neural phase oscillations of the brain which controls prolactin secretion levels comprising both (a) administering to the subject a dopamine agonist just after the time at which the normal prolactin profile peaks to reduce prolactin levels to the low "day" levels and (b) administering to the subject a prolactin stimulator at a time just before the prolactin level peaks in normal subjects with the objective of causing the subject's prolactin secretion profile to mimic in shape and time the profile of a lean human not suffering from one or more of aforementioned metabolic disorders.

Ser. No. 719,745 also discloses and claims the further administration of a thyroid hormone to subjects that are being treated with the dopamine agonist and prolactin stimulator, especially to those subjects that are chronically or seasonally hypothyroid.

Various aspects of the present invention have not been claimed in the foregoing applications. In addition, various improvements to and advantageous refinements of the administration protocol and its determination have now been made which increase the effectiveness of the treatment.

SUMMARY OF THE INVENTION

One aspect of this invention relates to a method for normalizing the daily prolactin release rhythm or profile of a first vertebrate subject in need of such treatment which comprises the steps of:

comparing the prolactin release profile of the first vertebrate subject to the prolactin release profile of other vertebrate subjects having a normal prolactin release profile; and adjusting the prolactin release profile of the first vertebrate subject to cause the profile of said first subject to generally conform to (or simulate) the prolactin release profile of said second subjects.

Another aspect of this invention relates to a method for evaluating the daily prolactin secretion profile of a human subject, which comprises the steps of:

(a) comparing the prolactin release profile of said subject, said profile having been determined over a continuous 24-hour period, to a predetermined standard prolactin release profile for healthy human subjects; and (b) determining whether said human. subject has an abnormal daily prolactin release rhythm by ascertaining whether (i) during waking hours the subject's prolactin secretion level is greater than 1 Standard Error of the Mean (SEM) above the mean prolactin secretion level of healthy subjects (a standard prolactin peak secretion level or a standard prolactin profile); and/or (ii) during Sleeptime the subject's prolactin level is at least 1 SEM lower than the mean of the prolactin profile of normal (healthy) individuals.

Yet another aspect of this invention relates to a method for determining whether adjustment will be required to "normalize" or generally conforman abnormal prolactin secretion profile to a standard (or healthy) prolactin secretion profile the method comprising: (a) collecting a plurality of blood samples from a subject over a continuous period, the collection of said samples being made at predetermined time intervals; (b) assaying the prolactin content of each of said samples; (c) plotting the prolactin content of each of said samples against the time at which said sample was collected during said continuous period to generate a plurality of data points (i.e. correlating the prolactin content with the time); (d) generating a prolactin profile by fitting a curve through said data points; and (e) comparing the prolactin profile to a predetermined normal prolactin profile. Steps (c) and (d) together constitute the step of expressing the prolactin content as a function of time to generate the prolactin profile of the subject.

Still another aspect of this invention relates to a method for determining adjustments that will cause an abnormal daily prolactin release rhythm of a patient to conform to a normal individual's daily prolactin release rhythm, which comprises: (a) comparing the prolactin release profile of the patient to a predetermined standard prolactin release profile for healthy (normal) subjects; (b) determining that (i) the prolactin level of said patient during waking hours exceeds the corresponding waking prolactin level of normal (healthy) individuals by at least 1 Standard Error of the mean (SEM) and/or determining that the prolactin level of such patient during Sleeptime is below the corresponding Sleeptime prolactin level of normal healthy individuals by at least one SEM; (c) determining the time at which to administer at least one member selected from the group consisting of a prolactin inhibitor and a prolactin stimulator to said subject; and (d) selecting the amount of said prolactin stimulator and/or inhibitor to adjust the subject's aberrant prolactin level such that the level is not greater than 1 SEM above the prolactin secretion profile of a normal healthy individual during waking hours and is no less than 1 SEM below the prolactin secretion profile of normal healthy individuals during Sleeptime.

BRIEF DESCRIPTION OF THE DRAWINGS

The present invention is further described with respect to the annexed drawings in which.

DETAILED DESCRIPTION OF THE INVENTION

All patents, patent applications and literature references cited herein are incorporated by reference in their entirety as if their disclosures were physically present in the present specification. In case of conflict, however, the present disclosure controls.

It has recently been discovered that metabolic disorders such as the foregoing are associated with aberrant patterns in the daily levels (and fluctuations) of prolactin secretion. Healthy (normal) subjects, i.e., lean members of a species not suffering from such metabolic abnormalities have highly predictable daily prolactin release profiles, which in humans are characterized by a low and relatively constant prolactin level during the waking hours (day) followed by a sharp rise to a peak during sleep (night) and subsequent more gradual tapering down to the waking hours level by morning.

In the present context "lean" means not obese and not abnormally underweight. In turn, an obese human is defined as a human whose body weight is over twenty percent above the ideal body weight for a given population (R. H. Williams, *Textbook of Endocrinology*, 1974, pp. 904–916). An abnormally underweight human is anyone at least 10% below his/her ideal bodyweight. Ideal body weight (IBW) can be determined by using the Metropolitan Life Insurance Company standard age/height/weight charts.

A prolactin release profile of a subject is obtained by collecting blood samples from the subject at timed intervals during a consecutive 24-hour time period (preferably at 3 hour intervals), assaying each blood sample for prolactin content, plotting the time of blood sampling against the quantity of prolactin present in each sample to generate a data point for each sample, and connecting the data points to form the prolactin release profile.

Although females generally have higher prolactin levels and sharper peaks than males, the shape of the normal prolactin profile for both sexes is qualitatively similar and does not vary appreciably from normal individual to normal individual (of the same sex) within the same species.

By contrast, individuals who suffer from one or more metabolic disorders have aberrant (often highly aberrant) daily prolactin secretion profiles. These prolactin profiles not only differ substantially from the norm but they can also differ from one another.

Figure 5:
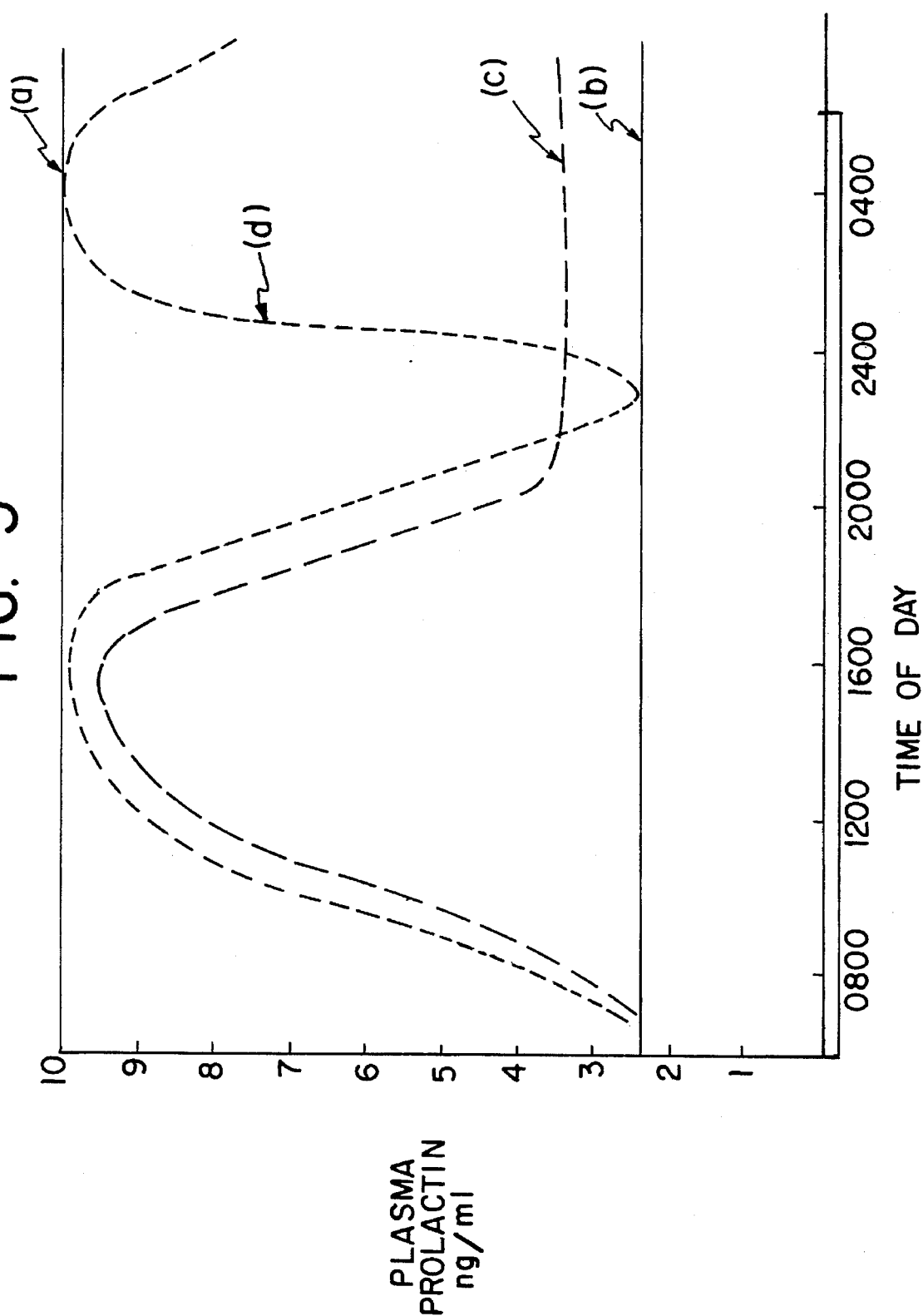
FIG. 5 is an illustrative superimposition of various types of typical human abnormal prolactin profiles identified by the letters (a) through (d).

The vast majority (at least about 80%) of patients with at least one of the foregoing metabolic disorders have abnormal daily prolactin release profiles that fall generally in one of four patterns represented schematically in FIG. 5:

(a) a flat (peak-free) high level (in this context "high" means higher than the "day" or waking hours prolactin level);

(b) a flat (peak-free) low level (in this context "low" means as low as or lower than the "day" or waking hours prolactin level);

(c) a peak during the "day" and a low level at "night" (in this context, "low" means low as compared to the normal average Sleeptime prolactin value between 0100 and 0400); and (d) a peak during the "day" and a second peak at "night".

"Waking hours" or "day" means the period of time at which in normal (healthy) humans (not working night shifts or alternate shifts) prolactin levels are relatively invariant and low (between 07:00 h and 22:00 h).

As employed herein the term "Sleeptime" or "night" means the period of time which in normal humans prolactin level rises to a peak (between 01:00 and 04:00) and then tapers off.

The normal average prolactin levels between the hours of 01:00 and 04:00 are between 8.0 and 14.0 nanograms/ml for males and between 14.0 and 26.0 nanograms/ml for females. See FIGS. 1–4.

"Prolactin inhibitor" shall include substances which directly or indirectly inhibit prolactin secretion in a subject (vertebrate animal or human). Nonlimiting examples of prolactin inhibitors include dopamine agonists such as dopamine and certain ergot-related prolactin-inhibiting compounds.

Nonlimiting examples of dopamine agonists are 2-bromo-alpha-ergocriptine; 6-methyl-8-beta-carbobenzyloxy-aminoethyl-10-alpha-ergoline; 8-acylaminoergolines, are 6-methyl-8-alpha-(N-acyl)amino-9-ergoline and 6-methyl-8-alpha-(N-phenylacetyl)amino-9-ergoline; ergocornine; 9,10-dihydroergocornine; and D-2-halo-6-alkyl-8-substituted ergolines, e.g., D-2-bromo-6-methyl-8-cyanomethyl-ergoline. Moreover, the non-toxic salts of the prolactin-inhibiting ergot-related compounds formed from pharmaceutically acceptable acids are also useful in the practice of this invention. Bromocriptine, or 2-bromo-alpha-ergocryptine, has been found particularly useful in the practice of this invention.

"Prolactin stimulator" shall include substances which directly or indirectly stimulate prolactin secretion. Nonlimiting examples of prolactin stimulators include dopamine antagonists such as metoclopramide, haloperidol, pimozide, phenothiazine, domperidone, sulpiride, chlorpromazine and serotonin agonists, i.e., MAO inhibitors, e.g., pargyline, synthetic morphine analogs, e.g., methadone, antiemetics, e.g., metoclopramide; antipsychotics, e.g., estrogens and others, e.g., tryptophan and 5-hydroxy-tryptophan. Moreover, the non-toxic salts of the foregoing prolactin stimulating compounds formed from pharmaceutically acceptable acids are also useful in the practice of this invention. Metoclopramide has been found particularly useful in the practice of this invention.

"Prolactin modulator" shall refer to either prolactin stimulators, prolactin inhibitors, or both.

DEVELOPMENT OF THE "NORMAL" PROLACTIN SECRETION PROFILE

A statistically significant number of healthy and young (20–35 years of age) humans are selected as follows:

All subjects are healthy and on normal diurnal work/rest schedule (no night guards or other night-shift workers). They are then divided into two different groups according to sex. All subjects must normally sleep between about 23:00 and about 07:00). The individuals are healthy in the sense that they are free of physiologic disorders or pathologies. In particular, they are not obese (based on standard age/size/weight tables); are known to have normal plasma levels of insulin; and are euthyroid i.e., have normal levels of plasma thyroxin, triiodothyronine, free-thyroxin and TSH.

A statistically significant number shall mean at least 3, the smallest sampling number for which statistical formulas generally have any meaning. However, a sampling number of at least 6 is generally preferred (at least 10 is more preferred) because this amount of sampling generally reduces the standard error (SE) of prolactin determinations.

Blood is collected from each subject at 3-hour intervals over a 24-hour period and, diurnal plasma levels of—prolactin, total triiodothyronine (T3) total thyroxin (T4), free-T4 and thyroid stimulating hormone (TSH) are measured for each subject for e.g., blood is collected over a 24-hour period at suitable time intervals (e.g., every three hours), typically starting at 10:00 am and finishing the next morning at 7:00 am).

Suitable sampling techniques and assay procedures are well-known to those skilled in the field and can be selected from published procedures, e.g., Linkowski, P. et al., *J. Clin. Endocrinol. Metab.* 61:429–438, 1985; Van Cauter and Copinschi, "Circadian and Episodic Variations", Martinus Nyhoff, The Hague Netherlands, pp. 1–25, 1981.

During sampling, all subjects must consume the same diet and maintain the same Sleeptime schedule.

Hormonal data, notably prolactin, from each blood sample plotted against time of day and a normal prolactin profile curve is developed including SEM.

(If desired, mathematical expressions can be developed to describe the area delineated by the curves.)

Figure 1:
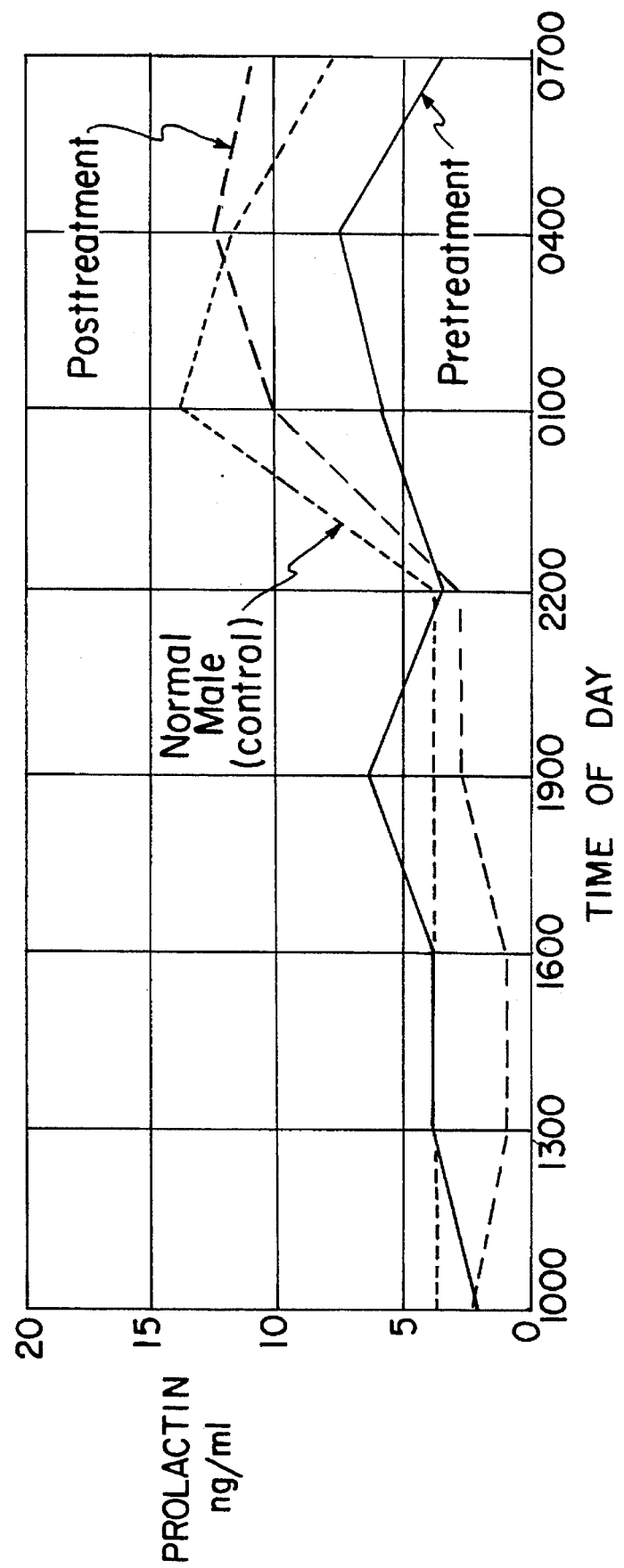
FIG. 1 is a superimposition of a male patient's abnormal base-level (pre-therapy) prolactin profile (thin black line) and interim (in-therapy) improved prolactin profile (thin grey line), and the standard normal prolactin profile (thick grey line), all in graph form. (Units are in nanograms per ml.)
Figure 2:
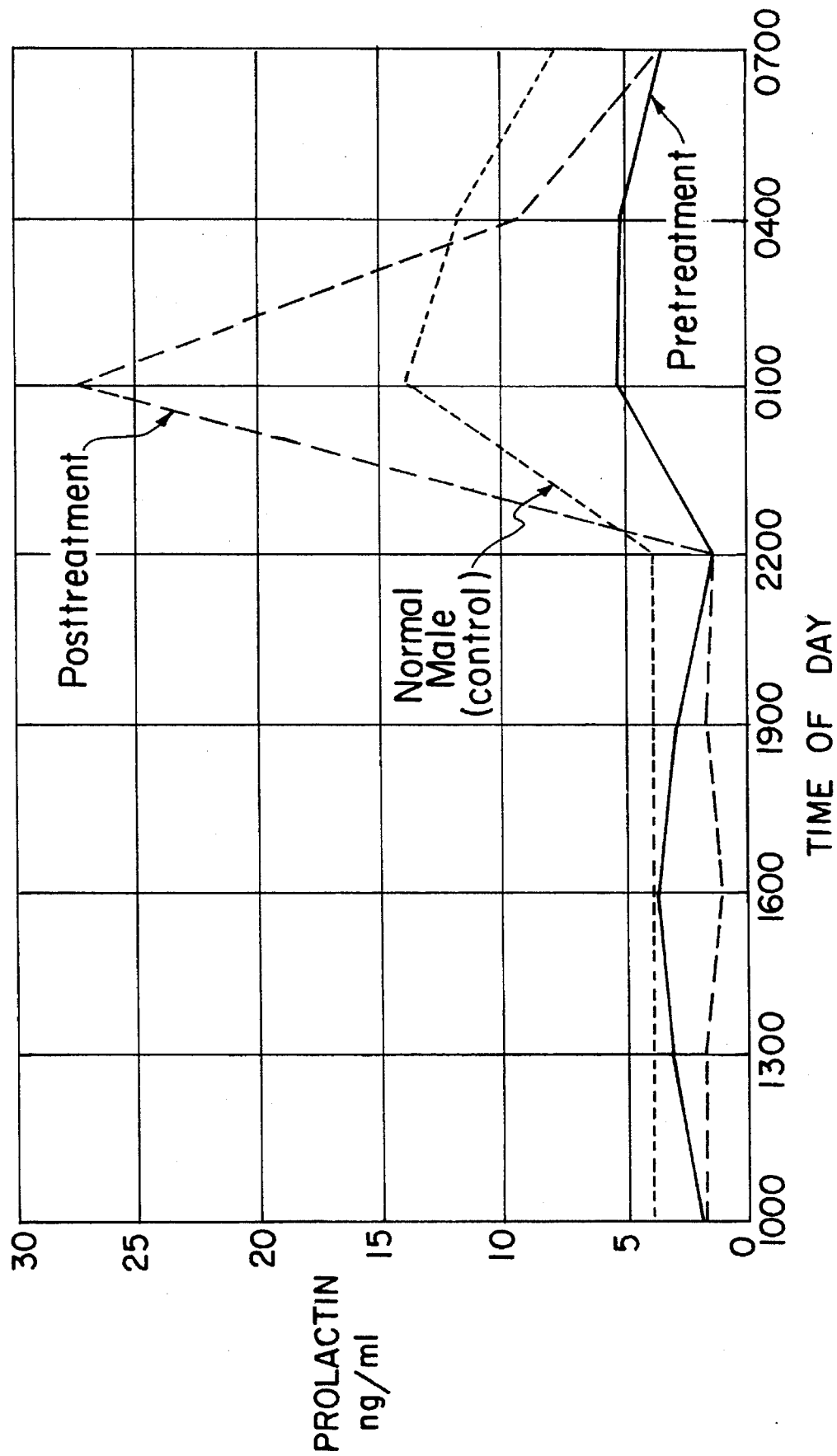
FIG. 2 is the same type of graphical superimposition as FIG. 1 for another male patient.

The result of such a normal profile development for males approximately 30 years of age is shown in FIGS. 1 and 2 depicted by the thick gray line. The result for females approximately 30 years of age is depicted by the thick gray line in FIGS. 3 and 4. The SEM (for prolactin in FIGS. 1–4) during waking hours for males is 1.0 to 2.0 nanograms per ml. and approximately 3.0 nanograms per ml. during Sleeptime. For females the SEM (for prolactin in FIGS. 1–4) during waking hours is between 1.0 and 3.0 nanograms per ml. and between 3.0 and 6.0 nanograms per ml. during Sleeptime.

DETERMINATION OF DIURNAL HORMONE PROFILE OF "AFFECTED" SUBJECTS

The procedure described above can be used to develop a prolactin profile for individuals under clinical evaluation for therapy according to the present invention. Individuals that are expected to have an abnormal daily prolactin profile include those having been diagnosed as afflicted with at least one of the following conditions: obesity (i.e., more than 20% overweight, based on age, frame size and sex characteristics using tables such as the Metropolitan Life Insurance Company tables for standard weight for height and age), insulin-resistant, hyperglycemic, hyperinsulinemic, hyperlipidemic, or suffering from Type II diabetes. However, the present evaluation is not limited to such subjects.

The subjects to be considered for therapy must be euthyroid, i.e., have a total T3 level between about 90 and about 180 ng/dl, total T4 between about 4.5 and about 12 μg/dl, and free-T4 between about 0.7 and about 1.8 μg/dl. If not, T4 and/or T3 needs to be administered prior to or concurrently with prolactin modulator administration preferably in the morning hours. In other words, it is not possible to adjust the prolactin release profile of an individual if his/her levels of T4 and/or T3 are low. Thus, prior to adjusting the prolactin profile of a subject through administration of a prolactin stimulator, or inhibitor, or both, it is necessary to determine that the subject has at least normal T3 and T4 (and preferably also free-T4) plasma levels. If the thyroid hormone level in a subject is below normal (as determined with reference to the above normal values) T3 and/or T4 are first administered to the subject until the plasma levels of these hormones are at or above normal and prolactin stimulatory or inhibitory treatment is then begun. The amount administered is the dosage required to bring the patient to a euthyroid condition; generally between about 25 and about 150 mcg per patient per day. If necessary to maintain adequate levels of T3/T4 throughout the period of administration of prolactin stimulator and/or inhibitor, T3/T4 can be continued along with the prolactin modulator therapy agents.

Once a diurnal prolactin level profile has been developed for an individual, it is compared to the "normal" profile, e.g., the one generated as described in the previous section. A determination is then made based on the following criteria:

1. From about 10:00 h to about 22:00 h, i.e., during the flat and low level portion of the "normal" prolactin profile, at a given point in the prolactin profile of the subject the prolactin value must not be higher than one SEM above the mean. This rule applies to exclude from a conclusion of "normal" all individual prolactin profiles that show at least one SEM above the mean in the day or below one SEM below the prolactin profile of normal healthy individuals during Sleeptime, as well as all individual prolactin profiles that throughout the 24-hour period are substantially uniformly too high or too low according to the one SEM criterion.

2. From about 22:00 h till about 07:00 h, i.e., during the rapid change (and Sleeptime peak) of the normal daily prolactin profile, the individual's prolactin profile must first have a peak at about the same time or within two to six hours after sleep initiation as the "normal" prolactin peak for subjects in the same category (usually about 01:00) and must also be within one SEM of the normal healthy prolactin profile.

To determine if a subject has an aberrant prolactin secretion profile the bedtime on the subject's prolactin release profile should be coincident with the bedtime on the profile of normal subjects. This is accomplished by superimposing the profile of the subject and the profile of normal individuals and shifting one or the other so that the sleep initiation time of the subject to be tested coincides with the sleep initiation time of normal healthy subjects.

DETERMINATION OF TREATMENT FOR AN AFFECTED SUBJECT

The information (prolactin secretion profile) generated as described above is used to (a) identify the patients that are in need of an adjustment in their prolactin secretion profile and (b) to determine the type and extent of adjustment required. In general, those individuals that are obese, hyperinsulinemic, hyperlipidemia, hyperglycemia or diabetic display abnormal prolactin secretion profiles as compared to healthy individuals. Simply stated, by comparing a subject's prolactin release profile with the standard prolactin release profile it is possible to identify individuals afflicted with the abnormal conditions discussed above. By adjusting the abnormal prolactin secretion profile of such individuals (either by administration of a prolactin inhibitor or a prolactin stimulator, or both) at the appropriate time of day and in the appropriate dosage (amount) it is possible to adjust such individuals prolactin profile to conform (or at least simulate) a normal release profile. The amount and timing of administration of such dosages can be determined based upon information contained in the prolactin release profiles discussed above.

The treatment determination has three aspects: (a) choice of medication (i.e., choice of prolactin stimulator or prolactin inhibitor, or both); (b) timing of (each) dose administration; and (c) amount of (each) dose to be administered. For example, if the patient is initially diagnosed as requiring a prolactin inhibitor, he might initially receive 0.8–1.6 mgs per day of bromocriptine in a single dose. The dosage might be adjusted after about 4 weeks of treatment e.g., at that time a fresh prolactin secretion profile would be taken and e.g., if the patient still had a high prolactin secretion level he would receive an increased dosage of a prolactin inhibitor at the appropriate time of day. The time of administration might also be adjusted (depending on the patient's current prolactin profile), e.g., the time of bromocriptine administration would be changed.

The comparison of the individual prolactin level profile to the normal prolactin profile will determine (a) and (b), as follows: If the "day" prolactin secretion level is too high (whether or not it has a peak), administration of a prolactin inhibitor is required.

If the "night" prolactin lacks a peak or if its peak is not sufficiently pronounced administration of a prolactin stimulator is required.

Generally, if a prolactin modulator is administered, it should be administered before it is needed and such that it produces its maximum effect on the prolactin daily rhythm when it is needed the most. As a practical matter, however, there is some latitude on the time of administration of the prolactin modulator. Moreover, administration of prolactin modulators during sleep should be avoided. The time of stimulator administration will be predetermined so that the maximum effect will coincide with the night prolactin peak.

The preferred prolactin inhibitor is bromocriptine and the preferred prolactin stimulator is metoclopramide. The average time for bromocriptine to exert its maximum prolactin inhibitory effect is between about 3 and about 4 hours after administration. The average time for metoclopramide to exert its maximum prolactin stimulating effect is about 2 hours from administration.

The following guidelines will generally be followed to initially determine bromocriptine or other prolactin inhibitor administration timing:

If prolactin peaks between 07:00 and 10:00, bromocriptine will be administered at 07:00;

If prolactin peaks between 10:01 and 16:00, bromocriptine will be administered at 08:00;

If prolactin peaks between 16:01 and 19:00, bromocriptine will be administered at 09:00;

If prolactin peaks between 19:01 and 22:00, bromocriptine will be administered at 10:00;

If prolactin peaks between 22:01 and 01:00, bromocriptine will be administered at 10:00;

If there is a prolactin peak between 01:01 and 07:00 do not administer bromocriptine.

If prolactin does not peak but is too high throughout waking hours bromocriptine is administered at 07:00.

If the average prolactin secretion between 01:00 and 04:00 is less than or equal to 8.0 ng/ml for men (or 14.0 ng/ml for women) then a prolactin stimulator will be administered.

The time schedules given above are intended as guidelines for bromocriptine administration and those skilled in the art can adjust the precise timing of bromocriptine administration based on the actual prolactin profile of a patient to be treated.

The time at which a different inhibitory or stimulatory agent is to be administered to a patient can be determined by ascertaining the time between administration of the agent and the time at which the agent exerts its maximum biological (i.e., stimulatory or inhibitory) effect. The time at which a stimulator has its maximum stimulating effect, (or when an inhibitor has its maximum inhibition effect) can be determined by administering the stimulatory or inhibitory drug to a patient with a known prolactin secretion profile and then calculating the time that elapses between administration of the drug and exertion of the maximum effect on movement (either inhibition or stimulation) of the patient's (known) prolactin secretion profile. Thereafter, the time of administration of the stimulator or inhibitor to the patient is adjusted so that the drug is administered to the patient sufficiently in advance of the point at which the patient's prolactin curve has the greatest deviation from the normal profile so that it will provide maximum effect at the point (time) at which the patient's profile deviates most from the normal profile. In fine tuning a subject's medication administration schedule the rebound effect that administration of a prolactin inhibitor during the day might have in Sleeptime prolactin levels of this subject should be taken into account. Conversely, the rebound effect that administration of a prolactin stimulator might have on prolactin levels during the subject's waking hours should also be considered. In this manner the time of administration for a particular inhibitor or stimulator can be determined using routine experimental procedures.

The precise time of modulator administration that will yield the most effective results in terms of efficacy of treatment in a given patient will depend upon the activity, pharmacokinetics, and bioavailability of a particular modulator, physiological conditions of the patient (including age, disease type and stage, physical condition, responsiveness to a given dosage and modulator), route of administration, etc. However, the above guidelines can be used as the basis for determining the optimum time of administration.

The foregoing are applicable for setting the initial therapy regimen. In general a patient receives between about 3 and about 100 micrograms of bromocriptine per kilogram of body weight per day, and preferably between about 10 and 40 micrograms per kg of body weight per day. The exact dosage of prolactin inhibitor (or prolactin stimulator) required to achieve the optimum effect in terms of prolactin secretion adjustment must be adjusted for each patient based upon the patient's drug sensitivity (i.e., response to drug) age, disease state and stage and physical condition. The patient is periodically reevaluated by measuring prolactin levels at predetermined intervals during a 24-hour period, the first such reevaluation typically occurring at the end of four weeks from the onset of therapy, and subsequent reevaluations occurring every 4 to 8 weeks during therapy and then every 3 months thereafter.

Prolactin stimulators are normally administered within about 1 hour prior to retiring for the patient's normal sleep period.

Adjustments to the amount(s) of drug(s) administered and possibly to the time of administration may be made as described above based on these reevaluations.

Generally, adjustment of timing and amount of drug(s) is not considered necessary if the Sleeptime prolactin peak during therapy is higher than normal as long as the peak value occurs at the right time, and the slopes of the peak are sharp (with normal values at each side of the normal peak).

The time at which it is desired to exert the maximum inhibitory or stimulatory effect on a particular patient (and therefore the appropriate time for administration) and the approximate amount (dosage range) for the degree of adjustment required can be determined by comparing the patient's abnormal (or reevaluation) prolactin release profile with the standard profile.

In treating vertebrates, generally, dosages of the prolactin inhibitor (bromocriptine) and/or stimulator (metoclopramide), respectively, are each given, generally once a day, generally over a period ranging from about 10 days to about 180 days. The preferred prolactin inhibitor (bromocriptine) is given daily at dosage levels ranging from about 3 micrograms to about 100 micrograms, preferably from about 10 micrograms to about 40 micrograms, per kg. of body weight, and the prolactin stimulator (metoclopramide) is given daily at dosage levels ranging from about 20 micrograms to about 200 micrograms, preferably from about 40 micrograms to about 100 micrograms, per kg. of body weight per day to modify, or alter, the prolactin secretion profile and continued for a time sufficient to reset the circadian plasma prolactin rhythm.

In treating humans, the prolactin inhibitor (bromocriptine) is generally given at daily dosage levels ranging from about 3 micrograms to about 100 micrograms, preferably from about 10 micrograms to about 40 micrograms, per kg. of body weight. The prolactin stimulator metaclopramide is generally given at daily dosage levels ranging from about 20 micrograms to about 200 micrograms, preferably from about 40 micrograms to about 100 micrograms, per kg. of body weight per day. Such treatment (using one or both types of drugs) is typically continued over a period of time ranging from about 10 days to usually about 180 days, resulting in modification and resetting of the lipid and glucose metabolism of the patient to that of a lean (i.e., normal) healthy person. For some patients (e.g. patients in particularly poor physical condition, or those of an advanced age) it may not be possible to reset their prolactin secretion profile within the above time periods and it is contemplated that such patients may require a longer, or even continuous, treatment with prolactin stimulators and/or inhibitors. The dosage and timing information set forth above is valid for bromocriptine and metaclopramide and will have to be altered for other agents using the dosage and timing guidelines disclosed herein.

In the practice of this invention, a prolactin-inhibiting compound, and a prolactin stimulator are administered daily to a subject preferably orally, or by subcutaneous, intravenous or intramuscular injection. Dermal delivery systems e.g., skin patches, as well as suppositories and other well-known systems for administration of pharmaceutical agents can also be employed.

Body fat deposits, inclusive of adipose, arterial wall and plasma fat, of an obese person will be reduced, leveled out and generally maintained (after the treatments of the present invention are discontinued) at that of a normal (lean) person, over an extended period of time. A subject that exhibits the effects of insulin resistance, hyperlipidemia or hyperinsulinemia and/or hyperglycemia, or both insulin resistance and hyperinsulinemia and/or hyperglycemia, treated with the prolactin inhibitor and/or a prolactin stimulator at the appropriate times of day discussed above, will become more sensitive to insulin (i.e., will have a lower insulin resistance), and the effects of hyperinsulinemia and/or hyperglycemia and related abnormal metabolic values will be reduced on a long termbasis. Treatment generally lasts between about 10 and about 180 days on average in humans. The administration of the prolactin inhibitor and/or prolactin stimulator in this manner will thus reset the phase relations of the two neural oscillations and their various circadian expressions to alter metabolism on a long term basis (e.g., several years), if not permanently. In other words, the result of the timed daily dosages of the prolactin inhibitor and/or prolactin stimulator will be a long term reversal of the major pathologies generally associated with the development of Type II diabetes. Using the methods of the present invention, the levels of body fat stores, plasma insulin concentrations, insulin resistance, and hyperglycemia, or all of these pathologies can be reduced on a long term basis by such treatment, or treatments, from the high levels often found in obese, hyperinsulinemic, hyperlipidemic and/or hyperglycemic persons to approach or conform to the much lower and much more desirable levels found in normal persons with normal insulin levels.

The following are non-limiting working examples of diagnosis, regimen determination and therapy according to the present invention:

Case Study 1: (E-04-M)

Subject: male; 73 yrs; 186 lbs; 5 ft 5 in.

Pathology:

(a) Obesity: 124% IBW (based on a standard Table, e.g., the standard table of Metropolitan Life Insurance Co. N.Y., N.Y. available from the company); body fat 26.48% (measured using caliper pinch method).

(b) Type II diabetes: fasting plasma glucose 237 mg; percent glycosylated hemoglobin 18.1% (measured by affinity chromatography); age at first diagnosis; 62. The normal morning fasting plasma glucose is between 80 and 120 mg percent (mg %).

The subject's 24-hour base (pre-therapy) prolactin profile is shown graphically as the black line in FIG. 1. It is a two peak pattern with the night peak being too low and occurring too late. The subject was given bromocriptine (3.2 mg) at 08:00 hr each day and metoclopramide (5 mg) at 23:00 hr each day for two consecutive weeks. A (reevaluation) prolactin profile was generated for the subject after four weeks and is graphically shown in FIG. 1 as the thin grey line.

The improvements observed in this patient were: (a) elimination of the day peak; (b) considerable increase of night prolactin peak and overall levels. The day prolactin level is somewhat low and the night peak still occurs too late. The clinical benefit of treatment to this patient included reduction in glycosylated hemoglobin from a starting level of 18.1% to 14.2% within 2 months of starting treatment. The patient's percent body fat was reduced from 26.48% to 21.78%; plasma cholesterol was reduced from 160 mg % to 140 mg %; triglycerides were reduced from 92 mg % to 79 mg %; fasting glucose was reduced from 237 mg % to 191 mg %; and oral glucose tolerance test results improved, all in the same 2 month period.

In all cases (FIGS. 1–4) visit 2 is one week before initiation of drug therapy. Visit 5 is after four weeks of drug therapy and visit 7 is after eight weeks of drug therapy.

Case Study 2: (E-10-M)

Subject: male; 73 yrs; 157 lbs; 5 ft. 4 in.

Pathology:

(a) Obesity: 114% IBW; body fat 23.72%

(b) Type II diabetes: fasting plasma glucose 269 mg %, glycosylated hemoglobin 14.7%; age at first diagnosis; 69.

On initial evaluation, the subject had the prolactin profile shown in FIG. 2 as the thin black line. The day prolactin level was lower than 1 SEM of the norm and the night peak was much too low (lower than SEM). The subject received 5 mg of metoclopramide at 23:00 daily and four weeks after the commencement of therapy another prolactin profile was generated (shown as the thin grey line in FIG. 2).

The second profile showed considerable improvement in both day and night prolactin levels. The fact that the night peak appears too high was considered perfectly acceptable because the curve is sharp and the peak occurs at the normal time. No adjustment to the regimen of this patient was made.

The clinical benefit of treatment to this patient included reduction in glycosylated hemoglobin from a starting level of 14.7% to 13.8% within 2 months of starting treatment. The patient's percent body fat was reduced from 23.72% to 21.52%; plasma cholesterol was reduced from 274 mg % to 266 mg %; triglycerides were reduced from 638 mg % to 583 mg %; and fasting glucose was reduced from 269 mg % to 218 mg %, all within the same 2 month period.

Case Study 3: (E-09-F)

Subject: female; 60 yrs; 182 lbs; 5 ft 6 in.

Pathology:

(a) Obesity: 132% IBW; body fat 42.48%

(b) Type II diabetes: fasting plasma glucose 359 mg; glycosylated hemoglobin 17.9%, age at first diagnosis; 45.

Figure 3:
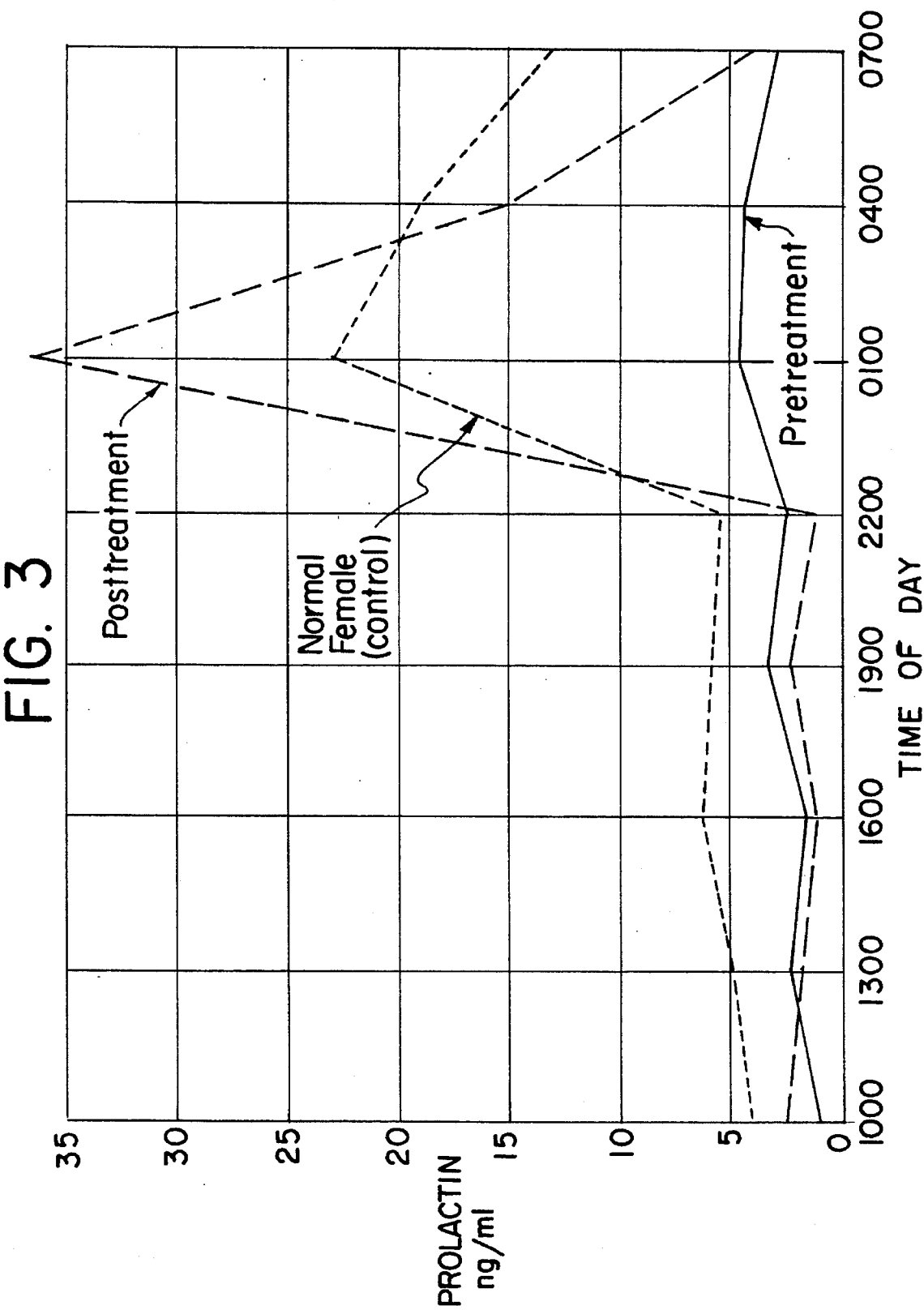
FIG. 3 is the same type of graphical superimposition as FIG. 1 for a female patient.

On initial evaluation, the subject had the prolactin profile shown by the thin black line in FIG. 3. Both the day and night prolactin levels were very low and there was virtually no prolactin peak. Four weeks after beginning daily administration of 5 mg metoclopramide at 23:00, the subject was re-evaluated (FIG. 3, thin grey line). Progress was considerable for the "night" prolactin profile. The day level remained low.

The clinical benefit of treatment to this patient included reduction in glycosylated hemoglobin from a starting level of 17.9% to 15.8% within 2 months of starting treatment. The patient's percent body fat was reduced from 42.48% to 41.29%; plasma cholesterol was reduced from 252 mg % to 218 mg %; triglycerides were reduced from 599 mg % to 259 mg %; fasting glucose was reduced from 359 mg % to 327 mg %; and oral glucose tolerance test results improved, all in the same 2 month period.

Case Study 4: (E-05-F)

Subject: female; 49 yrs; 211 lbs; 5 ft 4 in.

Pathology:

(a) Obesity: 146% IBW; body fat 46.81%

(b) Type II diabetes: fasting plasma glucose 325 mg; glycosylated hemoglobin 12.7%; age at first diagnosis; 39.

Figure 4:
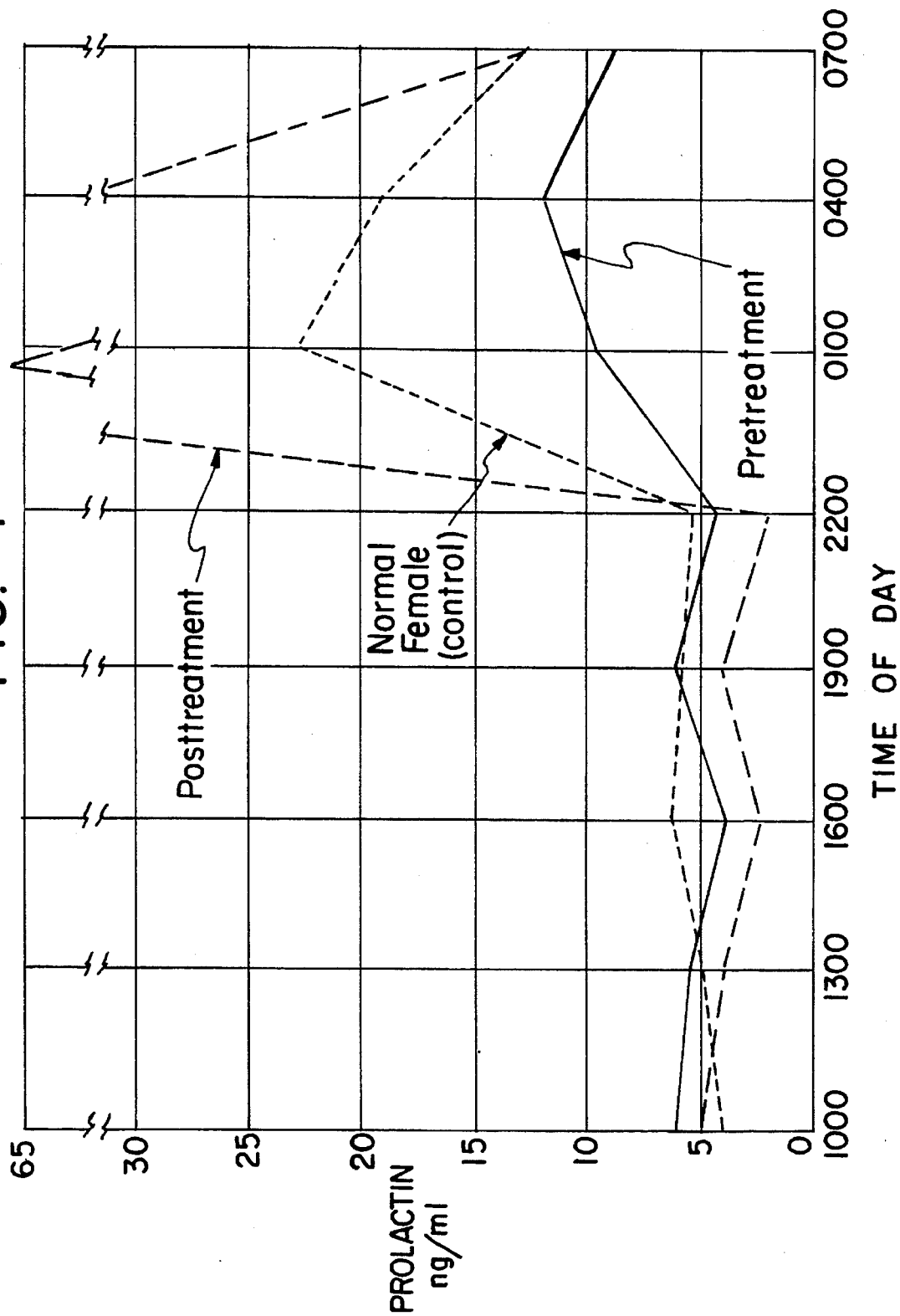
FIG. 4 is the same type of graphical superimposition as FIG. 1 for another female patient, except that FIG. 4 includes a second interim (in-therapy) prolactin profile for this patient (measured after eight weeks of treatment and depicted by the broken line).

On initial evaluation, the subject presented with the prolactin profile shown by the thin black line in FIG. 4. The day prolactin levels were acceptable but the night peak was too low and occurred too late. Four weeks after beginning daily administration of 5 mg metoclopramide at 23:00, the profile assumed the form of this thin grey line in FIG. 4. The prolactin peak was very high but the day level had visibly decreased.

The clinical benefit of treatment to this patient included reduction in glycosylated hemoglobin from a starting level of 12.7% to 12.1% within 2 months of starting treatment. The patient's percent body fat was reduced from 45.81% to 44.82%; plasma cholesterol was reduced from 215 mg % to 190 mg %; triglycerides were reduced from 280 mg % to 170 mg %; fasting glucose was reduced from 325 mg % to 267 mg %; and oral glucose tolerance test results improved, all in the same 2 month period.

In subsequent examples the terminology "LD" refers to the light/dark cycle, the first number following the expression LD refers to the hours of light, and the second to the hours of darkness in the cycle. Thus LD 14:10 refers to a cycle having 14 hours of light and 10 hours of darkness, and the period of a day is expressed in terms of 2400 hours. The letter n refers to the number of animals in a group, "BW" designates body weight, g represents grams and "ug" is an expression of micrograms. In the follow-up evaluations, the practitioner should bear in mind the rebound effects of prolactin stimulators or inhibitors. For instance, prolactin inhibition of abnormal daytime prolactin often has a "rebound" effect wherein low Sleeptime prolactin increases (even in the absence of prolactin stimulation). Also, prolactin stimulation of an abnormally low Sleeptime peak often results in reduction of abnormal high daytime prolactin levels (even in the absence of prolactin inhibition).

EXAMPLE 1

Adult female pigs, six in number, were given bromocriptine implants (10 mg/pig/day) over a period of time while being subjected to daily periods of daylight and darkness (12:12). Much of the implanted material enters the bloodstream at the start of the animals' activity period. A control group of six pigs were similarly treated to periods of daylight and darkness except that no bromocriptine was administered to the pigs of the control group. The period of darkness was from 1800 to 0600, and the period of daylight from 0600 to 1800. Daily tests were made of the blood of the pigs at four hour intervals over a 14 day period to determine the plasma cortisol level (ug/dl) and plasma prolactin level (ug/ml) of both groups. The average for each series of tests made on each group are given as follows:

| Time | Treated Pigs | Control |
|------|--------------|---------|
| Plasma Cortisol Level (ug/dl) | | |
| 0800 | 1.9 | 4.8 |
| 1200 | 1.5 | 3.4 |
| 1600 | 3.2 | 1.6 |
| 2000 | 2.8 | 1.9 |
| 2400 | 3.5 | 2.7 |
| 0400 | 3.2 | 5.5 |
| Plasma Prolactin Level (ug/ml) | | |
| 0800 | 1.8 | 0.5 |
| 1200 | 2.3 | 3.3 |
| 1600 | 2.8 | 1.3 |
| 2000 | 2.4 | 1.2 |
| 2400 | 2.3 | 1.7 |
| 0400 | 1.5 | 0.1 |

The effects of bromocriptine implants on fat stores and plasma concentrations of triglyceride, glucose and insulin are given as follows:

| Treatment | Backfat % control | Triglyceride mg/dl | Glucose mg/dl | Insulin Uv/ml |
|-----------|-------------------|--------------------|---------------|---------------|
| Control | 100 | 52 ± 8 | 99 ± 5 | 10.8 ± 1.8 |
| Bromocriptine (10 mg/day/pig) | 86$^3$ | 27 ± 3$^3$ | 86 ± 3$^3$ | 8.8 ± 0.3 |

Notes:
Backfat thickness was used as an index in determining fat stores. These data were obtained 28 days after treatment of the animals.
Plasma was sampled at 1600, 2000 and 2400 after two weeks of treatment. Each pig of the treatment group and control group was sampled.

These data clearly show that the bromocriptine implants altered the phase relationships of the circadian rhythms of plasma corticosteroid and prolactin concentrations, and produced changes beneficial to diabetics. The data show that, near sunset, when lipogenesis is normally greatest in pigs, bromocriptine reduced plasma triglyceride concentration by 48%. Since lipid is produced in the liver and transported in the blood to adipose tissue, the triglyceride reduction is further evidence that bromocriptine has an inhibitory effect on fat synthesis and deposition. In addition, although the reduction in plasma insulin concentration was not statistically significant, bromocriptine reduced plasma glucose levels by 13% during the early period of darkness (2000–2400). The reduction in blood glucose, without an increase in blood insulin concentration, can be explained as a decrease in insulin resistance (greater hypoglycemic responsiveness to insulin). Bromocriptine reduced body fat stores by 14% in the 28 day period of treatment.

Further studies were done on humans, these indicating that the symptoms of non insulin dependent, or Type II diabetes can be reduced by treatment with bromocriptine. Examples follow.

EXAMPLE 2

A 50 year old woman, showing the symptoms of diabetes, was daily given bromocriptine tablets (1.25–2.50 mg/day), taken orally, just after awakening. At the beginning of the treatment, blood glucose concentration was shown by routine testing to be near 250 mg/dl. In the weeks following the initial treatment, the patient's glucose levels fell to 180 mg/dl. to 155 mg/dl. to 135 mg/dl. to 97 mg/dl and to 101 mg/dl. Fasting levels below 120 mg/dl. are considered normal. Body weight and indices of body fat were also reduced about 12% by the treatment.

EXAMPLE 3

A 45 year old woman was being treated with a hypoglycemic agent (diabenase) which had reduced the blood glucose of the patient from 250 mg/dl to about 180 mg/dl during one year of treatment. Following daily oral administration of bromocriptine (parlodel, 1.25–2.5 mg/day), the blood glucose level fell dramatically to 80 mg/dl in 2 weeks. Removal of the hypoglycemic agent allowed glucose levels to rise and remain near 100 mg/dl (a normal level) in the succeeding two months. Body weight and fat were reduced about 10% by the bromocriptine treatment.

EXAMPLE 4

A 55 year old man weighing nearly 300 pounds was known to be a diabetic but had resisted all previous admonitions for treatment. At the beginning of oral bromocriptine treatment (parlodel, 2.5 mg/day), his plasma glucose concentration averaged near 350 mg/dl. During 2.5 months of bromocriptine treatment, body weight and plasma glucose concentration gradually but continuously decreased. Body weight has dropped 22 pounds and plasma glucose levels decreased to 160 mg/dl.

The data show that metabolic states are regulated at least in part by an interaction of circadian neuroendocrine rhythms. This hypothesis proposes that the daily rhythms of cortisol and prolactin are individual expressions of two separate circadian systems and that the daily injections of these hormones can reset the phase relations of these two systems. Thus, in a hamster model it has been found that the 0-hour relation resets the circadian oscillations into a pattern that maintains the lean, insulin sensitive state and the 12-hour relation permits retention of a pattern that maintains the obese, insulin resistant state. Another important addition of the present study is that the effects of timed injections of a dopamine agonist, or prolactin inhibiting compound, are long lasting. Apparently once reset, the phase relation of the two circadian oscillations tends to maintain its altered pattern.

Changes in the phase relations of two circadian neuroendocrine oscillations are evidenced by changes in the phase relations of their circadian expressions. This expectation is fulfilled respecting plasma glucocorticosteroid and prolactin rhythms. In several species examined, the phase relations of the two hormone rhythms differ in lean and fat animals.

The phase relation between the circadian rhythm of plasma insulin concentration and the rhythm of lipogenic responsiveness to insulin is shown to differ in lean and fat animals. Whereas the daily interval of lipogenic responsiveness remains near light onset, the phase of the insulin rhythm varies markedly. The peak concentration of insulin, e.g., occurs near light onset in obese female hamsters held on short day-lengths. That is, the daily peaks of the lipogenic stimulus (i.e., insulin) and the lipogenic response to insulin coincide in fat animals and not in lean animals.

It is apparent that various modifications and changes can be made without departing from the spirit and scope of this invention.

What is claimed:

1. A method for determining whether a vertebrate subject is in need of administration of a prolactin inhibitor or prolactin stimulator that will cause an abnormal daily prolactin rhythm to approach or conform to a healthy subject's daily prolactin rhythm, which comprises the steps of:
   a. measuring the prolactin blood level of the subject at spaced apart intervals during the vertebrate subject's waking hours and during the vertebrate subject's sleeptime over a time period of at least about 24 hours to generate a prolactin profile for said vertebrate subject;
   b. comparing said prolactin profile to a predetermined standard prolactin profile of healthy subjects of the same sex and species; and
   c. determining that
      (i) said subject should be administered a prolactin inhibitor in the event that the subject's prolactin level at any time during waking hours exceeds the prolactin level of healthy subjects during waking hours by more than 1 standard error of the mean; or that
      (ii) said subject should be administered a prolactin stimulator in the event that the subject's prolactin level any time during sleeptime is at least 1 standard error of the mean lower than the normal prolactin level of said healthy subjects during sleeptime.

2. The method of claim 1 wherein it is determined that said subject should be administered a prolactin stimulator.

3. The method of claim 1 wherein it is determined that said subject should be administered a prolactin inhibitor.

4. A method for determining whether a vertebrate subject is in need of administration of a prolactin inhibitor or prolactin stimulator that will cause an abnormal daily prolactin rhythm to approach or conform to a healthy subject's daily prolactin rhythm, which comprises the steps of:
   a. measuring the prolactin blood level of the subject at spaced apart intervals during the subject's waking hours and during the subject's sleeptime over a time period of at least about 24 hours to generate a prolactin profile for said subject;
   b. comparing the prolactin profile to a predetermined standard prolactin profile for healthy subjects of the same sex; and
   c. determining that
      (i) said subject should be administered a prolactin inhibitor in the event that the subject's prolactin level at any time during waking hours exceeds the prolactin level of healthy subjects during waking hours by more than 1 standard error of the mean; or that
      (ii) said subject should be administered a prolactin stimulator in the event that the subject's prolactin level any time during sleeptime is at least 1 standard error of the mean lower than the normal prolactin level of said healthy subjects during sleeptime.

5. The method of claim 4 wherein said subject suffers from Type II diabetes.

6. The method of claim 4 wherein said subject suffers from obesity.

7. The method of claim 4 wherein said subject suffers from hyperlipidemia.

8. The method of claim 4 wherein it is determined that said subject should be administered a prolactin stimulator.

9. The method of claim 4 wherein it is determined that said subject should be administered a prolactin inhibitor.

10. The method of claim 4 wherein it is determined that said subject should be administered both a prolactin stimulator and a prolactin inhibitor.

11. A method for determining whether a vertebrate subject is in need of administration of a prolactin inhibitor or prolactin stimulator that will cause an abnormal daily prolactin rhythm to approach or conform to a healthy subject's daily prolactin rhythm, which comprises the steps of:
   a. comparing a prolactin profile of said subjects being tested that has been compiled over a predetermined period of about 24 hours to a predetermined standard prolactin profile for healthy human subjects; and
   b. determining that
      (i) said subject should be administered a prolactin inhibitor in the event that the subject's prolactin level at any time during waking hours exceeds the prolactin level of healthy subjects during waking hours by more than 1 standard error of the mean; or that
      (ii) said subject should be administered a prolactin stimulator in the event that the subject's prolactin level any time during sleeptime is at least 1 standard error of the mean lower than the normal prolactin level of said healthy subjects during sleeptime.

12. The method of claim 11 wherein said subject suffers from Type II diabetes.

13. The method of claim 11 wherein said subject suffers from obesity.

14. The method of claim 11 wherein said subject suffers from hyperlipidemia.

15. A method for determining whether a vertebrate subject is in need of administration of a prolactin inhibitor or prolactin stimulator that will cause an abnormal daily prolactin rhythm to approach or conform to a healthy subject's daily prolactin rhythm, which comprises the steps of:
   comparing a prolactin profile of said subject being tested, said profile having been determined within a period of time of about 24 hours, to a predetermined standard prolactin profile for healthy individuals; and
   b. determining that
      (i) said subject should be administered a prolactin inhibitor in the event that the subject's prolactin level at any time during waking hours exceeds the prolactin level of healthy subjects during waking hours by more than 1 standard error of the mean; or that
      (ii) said subject should be administered a prolactin stimulator in the event that the subject's prolactin level any time during sleeptime is at least 1 standard error of the mean lower than the normal prolactin level of said healthy subjects during sleeptime.

16. The method of claim 15 wherein said subject suffers from Type II diabetes.

17. The method of claim 15 wherein said subject suffers from obesity.

18. The method of claim 15 wherein said subject suffers from hyperlipidemia.

19. A method for normalizing the daily prolactin rhythm in a subject having an abnormal prolactin daily rhythm which comprises the steps of:
   comparing the prolactin profile of said subject to the prolactin profile of healthy subjects of the same species and sex; and
   adjusting the prolactin profile of said subject having an abnormal prolactin daily rhythm to generally approach or conform said abnormal rhythm to the prolactin profile of said healthy subjects;

wherein said adjusting step comprises at least one of:

administering to said subject having an abnormal prolactin daily rhythm a predetermined amount of a prolactin inhibitor at a first predetermined time prior to a time at which said subject's daytime prolactin level is higher than said healthy subjects' prolactin level by more than 1 standard error of the mean; and administering to said subject having an abnormal prolactin daily rhythm a predetermined amount of a prolactin stimulator at a second predetermined time prior to a time at which said subject's sleeptime prolactin level is lower than said healthy human subjects' prolactin level by at least 1 standard error of the mean.

20. The method of claim 19 wherein said subject suffers from Type II diabetes.

21. The method of claim 19 wherein said subject suffers from obesity.

22. The method of claim 19 wherein said subject suffers from hyperlipidemia.

23. The method of claim 19 wherein said prolactin inhibitor is bromocriptine.

24. The method of claim 19 wherein said prolactin stimulator is metoclopramide.

25. The method of claim 20 wherein said prolactin inhibitor is bromocriptine.

26. The method of claim 20 wherein said prolactin stimulator is metoclopramide.

27. The method of claim 19 wherein said prolactin stimulator is 5-hydroxytryptophan.

28. The method of claim 20 wherein said prolactin stimulator is 5-hydroxytryptophan.

29. A method for determining administration that will cause an abnormal daily prolactin rhythm of a patient to approach or conform to a healthy subject's daily prolactin rhythm, which comprises:

a. comparing the prolactin profile of said patient to a predetermined standard prolactin profile for normal subjects;

b. determining that said patient should be administered a prolactin inhibitor in the event that the patient's prolactin level at any time during waking hours exceeds the prolactin level of healthy subjects during waking hours by more than 1 standard error of the mean;

c. selecting a time for administration of said prolactin inhibitor that is no later than the time at which the waking hours prolactin level of said patient reaches the highest waking hours level; and d. selecting the amount of said prolactin inhibitor to be administered to said patient so that the prolactin level of said patient at any time during waking hours is not greater than 1 standard error of the mean above the prolactin level of said healthy subjects.

30. The method of claim 29 wherein said subject suffers from Type II diabetes.

31. The method of claim 29 wherein said subject suffers from obesity.

32. The method of claim 29 wherein said subject suffers from hyperlipidemia.

33. The method of claim 29 wherein said prolactin inhibitor is bromocriptine.

34. The method of claim 30 wherein said prolactin inhibitor is bromocriptine.

35. A method for determining administration that will cause an abnormal daily prolactin rhythm of a subject to approach or conform to the daily prolactin rhythm of a healthy subject, comprising:

a. comparing the prolactin profile of said subject having an abnormal prolactin rhythm to a predetermined standard prolactin profile for healthy subjects;

b. determining that said subject having an abnormal prolactin rhythm is in need of a prolactin stimulator by ascertaining that the prolactin level of said subject at any time during sleeptime is at least 1 standard error of the mean lower than the normal prolactin level of said healthy subjects during sleeptime;

c. selecting the timing of administration of said prolactin stimulator to said subject having an abnormal prolactin rhythm to be prior to the time at which the sleeptime prolactin level reaches its peak in healthy subjects; and d. selecting an amount of said prolactin stimulator to be administered to said subject having an abnormal prolactin rhythm such that the prolactin level of said subject at any time during sleeptime is no lower than 1 standard error of the mean below the normal prolactin profile of said healthy subjects during sleeptime.

36. The method of claim 35 wherein said subject suffers from Type II diabetes.

37. The method of claim 35 wherein said subject suffers from obesity.

38. The method of claim 35 wherein said subject suffers from hyperlipidemia.

39. The method of claim 35 wherein said prolactin stimulator is metoclopramide.

40. The method of claim 36 wherein said prolactin stimulator is metoclopramide.

41. The method of claim 35 wherein said prolactin stimulator is 5-hydroxytryptophan.

42. The method of claim 36 wherein said prolactin stimulator is 5-hydroxytryptophan.

43. A method for determining whether a human subject is in need of administration of a prolactin inhibitor or prolactin stimulator that will cause an abnormal daily prolactin rhythm to approach or conform to a healthy subject's daily prolactin rhythm, comprising:

a. collecting a plurality of blood samples from said human subject at spaced apart time intervals within a period of time of about 24 hours;

b. measuring the prolactin content of each of said samples;

c. plotting the prolactin content of each of said samples against the time at which said sample was collected during said time period to generate a data point;

d. generating a prolactin profile by connecting each of said data points with the adjacent data point immediately following it;

e. comparing said prolactin profile to a predetermined standard prolactin profile for healthy subjects; and f. determining that (i) said subject should be administered a prolactin inhibitor in the event that the subject's prolactin level at any time during waking hours exceeds the prolactin level of healthy subjects during waking hours by more than 1 standard error of the mean; or that (ii) said subject should be administered a prolactin stimulator in the event that the subject's prolactin level any time during sleeptime is at least 1 standard error of the mean lower than the normal prolactin level of said healthy subjects during sleeptime.

44. The method of claim 43 wherein said subject suffers from Type II diabetes.

45. The method of claim 43 wherein said subject suffers from obesity.

46. The method of claim 43 wherein said subject suffers from hyperlipidemia.

47. A method for determining whether a human subject is in need of administration of a prolactin inhibitor or prolactin stimulator that will cause an abnormal daily prolactin rhythm to approach or conform to a healthy subject's daily prolactin rhythm, which comprises the steps of:
  a. measuring the prolactin blood level of the subject at spaced apart intervals during the subject's waking hours and during the subject's sleeptime over a time period of at least about 24 hours to generate a prolactin profile for said subject;
  b. comparing said prolactin profile to a predetermined standard prolactin profile of healthy subjects of the same sex; and
  c. determining that
    (i) said subject should be administered a prolactin inhibitor in the event that the subject's prolactin level at any time during waking hours exceeds the prolactin level of the normal control of FIG. 1, if said subject is a male, or the normal control of FIG. 3, if said subject is a female, by more than 1 standard error of the mean; or that
    (ii) said subject should be administered a prolactin stimulator in the event that the subject's prolactin level any time during sleeptime is at least 1 standard error of the mean lower than the prolactin level of healthy subjects of the same sex as said subject.

48. A method for determining whether a human subject is in need of administration of a prolactin inhibitor or prolactin stimulator that will cause an abnormal daily prolactin rhythm to approach or conform to a healthy subject's daily prolactin rhythm which comprises:
  a. determining prolactin levels in blood samples that were taken from said subject over a time period of at least about 24 hours to generate a prolactin profile for said subject;
  b. comparing said prolactin profile to a predetermined standard prolactin profile for healthy human subjects;
  c. determining that
    (i) said subject should be administered a prolactin inhibitor in the event that the subject's prolactin level at any time during waking hours exceeds the prolactin level of healthy subjects during waking hours by more than 1 standard error of the mean; or that
    (ii) said subject should be administered a prolactin stimulator in the event that the subject's prolactin level any time during sleeptime is at least 1 standard error of the mean lower than the normal prolactin level of said healthy subject during sleeptime.

* * * * *